United States Patent
Epstein et al.

(10) Patent No.: US 6,656,207 B2
(45) Date of Patent: Dec. 2, 2003

(54) EXPANSILE DEVICE FOR USE IN BLOOD VESSELS AND TRACTS IN THE BODY AND METHOD

(75) Inventors: Gordon H. Epstein, Fremont, CA (US); Todd E. Lempert, Piedmont, CA (US); Brian B. Martin, Boulder Creek, CA (US); David M. Taylor, Fremont, CA (US); Richard M. Romley, Alameda, CA (US)

(73) Assignee: Biointerventional Corporation, Pleasanton, CA (US)

( * ) Notice: Subject to any disclaimer, the term of this patent is extended or adjusted under 35 U.S.C. 154(b) by 0 days.

(21) Appl. No.: 10/272,508

(22) Filed: Oct. 15, 2002

(65) Prior Publication Data

US 2003/0163146 A1 Aug. 28, 2003

Related U.S. Application Data

(63) Continuation of application No. 09/528,574, filed on Mar. 20, 2000, now Pat. No. 6,464,712, which is a continuation-in-part of application No. 09/241,680, filed on Feb. 1, 1999, now Pat. No. 6,056,770, which is a continuation-in-part of application No. 08/972,383, filed on Nov. 18, 1997, now Pat. No. 5,922,009, which is a continuation-in-part of application No. 08/798,870, filed on Feb. 11, 1997, now Pat. No. 5,782,860.

(51) Int. Cl.⁷ .............................................. A61B 17/08
(52) U.S. Cl. ....................................................... 606/213
(58) Field of Search ................................ 606/213, 215

(56) References Cited

U.S. PATENT DOCUMENTS

| | | |
|---|---|---|
| 4,744,364 A | 5/1988 | Kensey |
| 4,852,568 A | 8/1989 | Kensey |
| 4,890,612 A | 1/1990 | Kensey |
| 5,108,421 A | 4/1992 | Fowler |
| 5,171,259 A | 12/1992 | Inoue |
| 5,258,000 A | 11/1993 | Gianturco |
| 5,383,896 A | 1/1995 | Gershony et al. |
| 5,419,765 A | 5/1995 | Weldon et al. |
| 5,454,833 A | 10/1995 | Boussignac et al. |
| 5,626,601 A | 5/1997 | Gershony et al. |
| 5,630,833 A * | 5/1997 | Katsaros et al. ............ 606/213 |
| 5,634,936 A * | 6/1997 | Linden et al. ............... 606/213 |
| 5,861,003 A | 1/1999 | Latson et al. |
| 5,868,778 A | 2/1999 | Gershony et al. |
| 5,951,583 A | 9/1999 | Jensen et al. |
| 5,957,952 A | 9/1999 | Gershony et al. |
| 6,017,359 A | 1/2000 | Gershony et al. |

OTHER PUBLICATIONS

Datascope Corporation, "VasoSeal" product brochure, 1991.
Sherwood, Davies & Geck, "AngioSeal" product brochure, 1977.

* cited by examiner

*Primary Examiner*—Gary Jackson
(74) *Attorney, Agent, or Firm*—Townsend and Townsend and Crew LLP

(57) ABSTRACT

A device for expansion within a blood vessel having a wall defining a lumen in the body. The device comprises an elongated tubular member having proximal and distal extremities and having a longitudinal axis. An expansile member is carried by the distal extremity of the elongated tubular member and is movable between contracted and expanded configurations. A deformable membrane having proximal and distal outer surfaces at least partially covers the expansile member in the expanded configuration. The proximal and distal outer surfaces have substantially different configurations when the expansile member is in the expanded configuration. Deployment means is carried by the proximal extremity of the elongated tubular member and is coupled to the expansile member for moving the expansile member between the contracted and expanded configurations. A handle assembly is carried by the proximal extremity of the elongated tubular member and coupled to said deployment means.

8 Claims, 4 Drawing Sheets

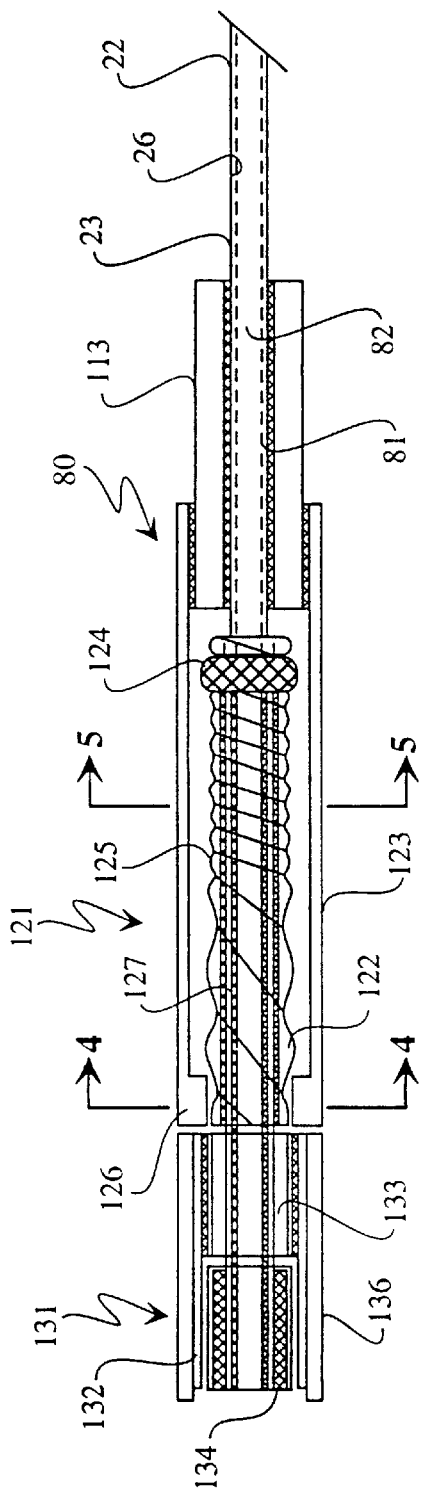
FIG. 3
FIG. 4
FIG. 5

EXPANSILE DEVICE FOR USE IN BLOOD VESSELS AND TRACTS IN THE BODY AND METHOD

This is a continuation of application Ser. No. 09/528,574 filed Mar. 20, 2000, now U.S. Pat. No. 6,464,712 which is a continuation-in-part of prior application Ser. No. 09/241,680, filed Feb. 1, 1999 which is a continuation-in-part of application Ser. No. 08/972,383, filed Nov. 18, 1997 which issued as U.S. Pat. No. 5,922,009 on Jul. 13, 1999, which is a continuation-in-part of application Ser. No. 08/798,870, filed Feb. 11, 1997 which issued as U.S. Pat. No. 5,782,860 on Jul. 21, 1998.

This invention relates to an expansile device for use in vascular access tracts and non-vascular tracts in the human body and method and more particularly for percutaneous occlusion of vascular access sites in the human body.

Percutaneous access to the blood vessels and organs of the human body for diagnosis and treatment of disease processes has heretofore been accomplished.

Percutaneous vascular procedures are performed involving the coronary, peripheral and cerebral vasculature. These procedures include coronary and peripheral angiography, angioplasty, atherectomies, coronary retroperfusion and retroinfusion, cerebral angiograms, treatment of strokes, cerebral aneurysms and the like. Patients undergoing such procedures are often treated with anti-platelet drugs, anti-coagulants such as heparin, thrombolytics, or a combination thereof, all of which interfere with coagulation making it more difficult for the body to seal a puncture site. Various devices and methods have heretofore been utilized, however, they all have had deficiencies, including the use of complicated devices and methods. In addition, difficulties are still encountered in obtaining good seals. There is therefore a need for a device and method for percutaneous access and occlusion of vascular access sites and other puncture sites and natural tracts in the human body which overcome the deficiencies of prior art devices and methods.

In general, it is an object of the present invention to provide an expansile or closure device and method for percutaneous access and occlusion of vascular access sites, other puncture sites and natural tracts involving various organs having lumens or cavities in the human body which will make possible a positive seal of the puncture site or tract promoting rapid healing of the puncture site or tract.

Another object of the invention is to provide a closure device and method of the above character which can be easily and reliably used.

Another object of the invention is to provide a closure device and method of the above character which permits easy placement of the device without measuring or sizing of the tract or device.

Another object of the invention is to provide a closure device and method of the above character which can be deployed or made operative with one maneuver or movement.

Another object of the invention is to provide a closure device and method of the above character which can be deployed and is effective in severely tortuous vessels.

Another object of the invention is to provide a closure device and method of the above character which enables continued substantially unobstructed blood flow during deployment and use of the closure device.

Another object of the invention is to provide a closure device and method of the above character in which no foreign body remains in the blood vessel.

Another object of the invention is to provide a closure device and method of the above character that permits early ambulation of patients and avoids prolonged bed rest.

Another object of the invention is to provide a closure device and method of the above character which reduces the risk of bleeding, formation of arteriovenous fistula, formation of pseudoaneurysm, thrombosis with distal embolization and infection.

Another object of the invention is to provide a closure device and method of the above character that reduces the risk of causing ischemia of an extremity.

Another object of the invention is to provide a closure device and method of the above character that is inexpensive, quick, safe, easy to use and is disposable.

Additional objects and features of the invention will appear from the following description in which the preferred embodiments and the methods using the same are described in conjunction with the accompanying drawings.

FIG. 3 is an exploded side-elevational view in section showing the handle assembly and stop mechanism of the device of FIGS. 1–2.

FIG. 4 is a cross-sectional view taken along the line 4—4 of FIG. 3.

FIG. 5 is a cross-sectional view extending distally for several millimeters taken along the line 5—5 of FIG. 3.

Figure 8B:
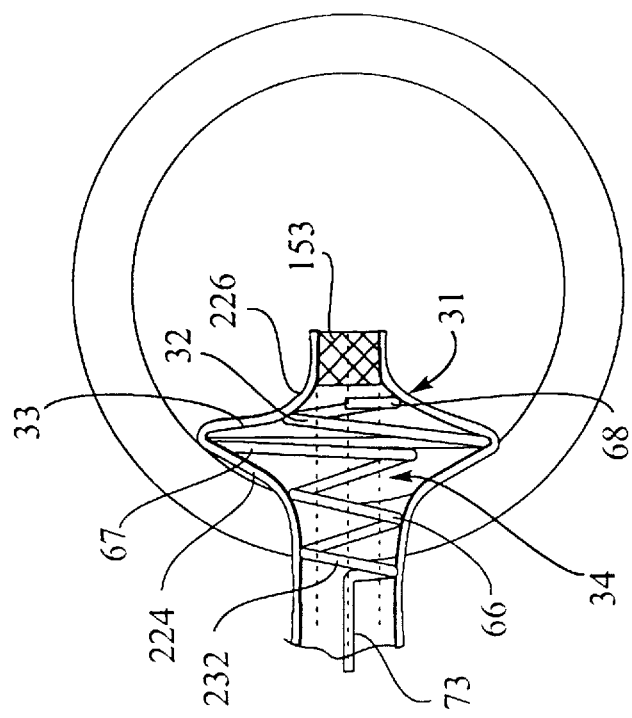
Figure 8A:
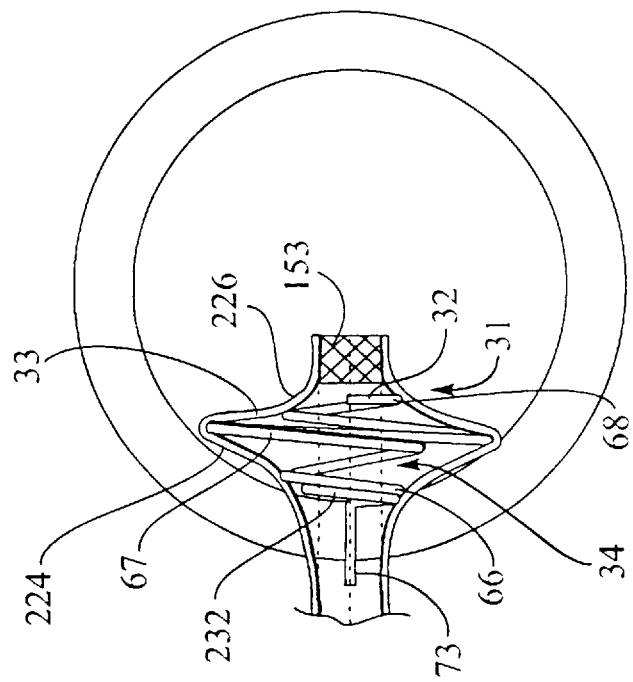

FIGS. 8a and 8b are exploded cross-sectional views of the distal extremity of another embodiment of the device of the present invention showing the expansile assembly in the expanded configuration occluding a puncture in a blood vessel. FIG. 8a shows the expansile assembly of the device without proximal tension applied thereto and FIG. 8b shows the expansile assembly of the device with proximal tension applied thereto.

In general, the device for expansion within an organ having a wall defining a lumen or cavity in the body of the present invention comprises an elongated tubular member having proximal and distal extremities and having a longitudinal axis. An expansile member is carried by the distal extremity of the elongated tubular member and is movable between contracted and expanded configurations. A deformable membrane at least partially covering the expansile member is sized so as to be capable of expanding as the expansile member moves from the contracted configuration to the expanded configuration. Deployment means are carried by the proximal extremity of the elongated tubular member and coupled to the expansile member. The deployment means are adapted to be capable of moving the expansile member between the contracted and expanded configurations. A handle assembly is carried by the proximal extremity of the elongated tubular member and coupled to the deployment means.

Figure 1:
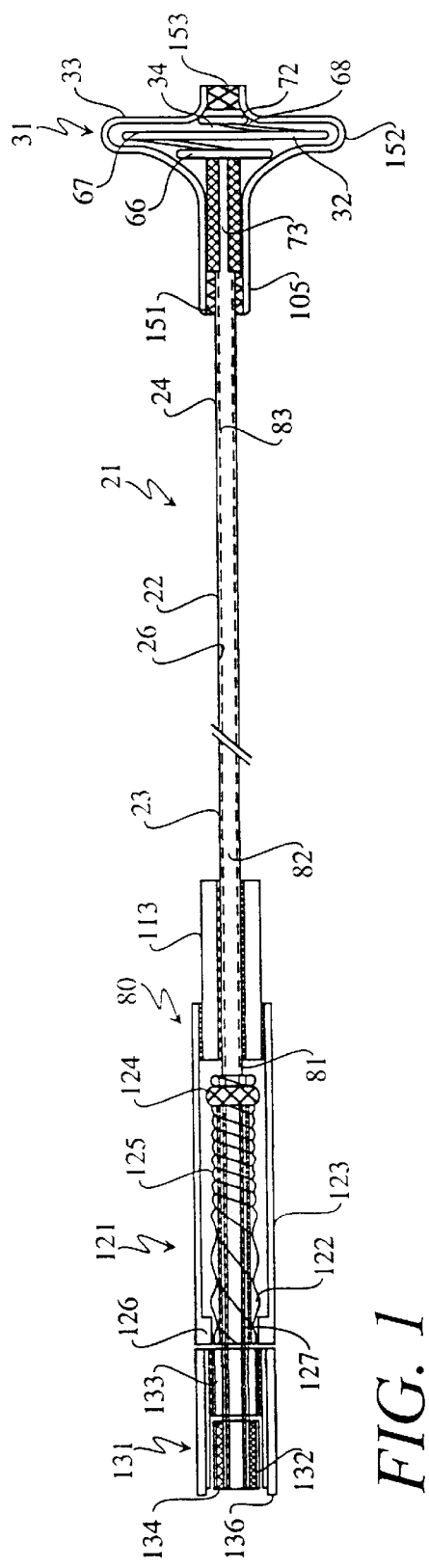
FIG. 1 is a side-elevational view partially in section of an expansile or closure device for obtaining percutaneous access and occlusion of tracts and punctures in the human body incorporating the present invention without the tip guide and having the expansile member in a deployed or expanded position.
Figure 2:
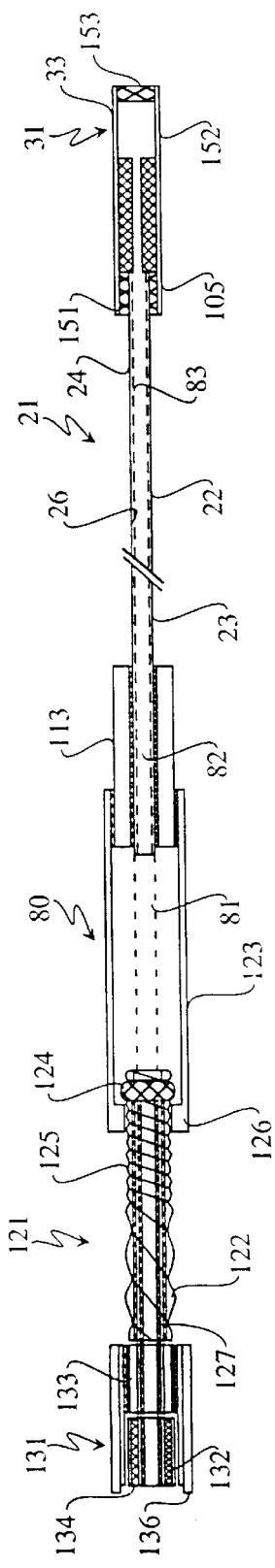
FIG. 2 is a side-elevational view partially in section of the device in FIG. 1 with the expansile assembly in a de-deployed or contracted configuration.

More specifically, as shown in FIGS. 1–2, the expansile device 21 of the present invention comprises a first elongate tubular member 22, preferably a flexible elongate tubular member 22, formed of a suitable plastic material, preferably a cast thermoset material such as polyimide. The inner and outer surfaces of the polyimide material may be coated with a lubricious material such as Teflon™. Alternatively, the thermoset material may be a polyimide-Teflon™ composite in order to provide the desired lubricious inner and outer surfaces. The first flexible elongate tubular member 22 has proximal and distal extremities 23 and 24 with a longitudinal axis extending from the proximal 23 to the distal extremity 24 and is provided with a first lumen 26 circular in cross-section which, as shown, may be centrally disposed extending from the proximal extremity 23 to the distal extremity 24.

The flexible elongate tubular member 22 is of a suitable size, as for example having an outer diameter ranging from 1–9 French corresponding to an outer diameter ranging from approximately 0.008" to 0.050", preferably approximately 0.022"–0.026", and a suitable length, as for example 10–150 centimeters, preferably 33 centimeters ±1 centimeter. The first lumen 26 in the first flexible elongate tubular member 22 may have an inside diameter of approximately 0.003" to 0.030", preferably 0.012"–0.014".

Expansile means in the form of an expansile assembly 31 is carried by the distal extremity 24 of the flexible elongate tubular member 22 and is movable between contracted and expanded positions. A deployment mechanism is carried by the proximal extremity 23 of the flexible elongate tubular member 22 and adapted to be operated by the human hand for movement from a contracted position or configuration to an expanded position or configuration.

The expansile assembly 31 includes an expansile member 32 and a membrane 33 which at least partially covers the expansile member 32. As shown in FIG. 2, the expansile member 32 is in a form having a complex geometrical configuration, preferably a ellipsoidal, helical or bi-conical coil configuration 34, when in the free, unconstrained state. As hereinafter discussed, the helical coil 34 is formed of a suitable material such as a shape memory or superelastic material which can be elongated, contracted or constrained without permanent deformation but, at body temperature, when freed or unconstrained returns to the memorized helical coil configuration 34 to which it has been annealed. One material found to be particularly suitable for such an application is a nickel/titanium alloy wire, often called Nitinol™ wire.

The correctly annealed and configured helical coil 34 has a plurality of generally circular turns, loops or coils creating, preferably, a proximal coil, loop or turn 66, a middle coil, turn or loop 67 and a distal coil, turn or loop 68 as shown in FIG. 1. The proximal, middle and distal coils 66, 67 and 68 are generally nonplanar with respect to one another. At least a portion of the proximal coil 66 and a portion of the distal coil 68 each lie in a plane that is generally parallel to one another and generally perpendicular to the longitudinal axis of the flexible elongate tubular member 22. The middle coil 67 is non-planar and helical as it connects the proximal and distal coils 66 and 68 so that the unconstrained or free helical coil 34 assumes a substantially ellipsoidal or bi-conical shape.

The middle coil 67, when freed or unconstrained, has a suitable diameter ranging from 3 to 10 millimeters, preferably, greater than or equal to 5.33 millimeters (16 French). As hereinafter discussed, during deployment the middle coil 67 is partially flattened and constrained by the membrane 33 to maintain a diameter of approximately 16 French in order to overlap a puncture site or other opening to assist in occluding the opening. The proximal and distal coils 66 and 68 are of approximately equal size and diameter ranging from 1 to 5 millimeters, preferably 2 to 3 millimeters. The unconstrained helical coil 34 configuration has a distance from the proximal 66 to the distal 68 coil of approximately 4–8 millimeters. As hereinafter discussed, the helical coil 34 is retracted into the flexible elongate tubular member 22 to obtain the de-deployed configuration wherein the contracted, constrained diameter corresponds to the approximate diameter of the Nitinol wire used to construct the expansile member 32, ranging from 0.002" to 0.010", preferably 0.0055". As hereinafter discussed, the expansile member 32 is provided with a straight portion 73 of Nitinol wire proximal to the helical coil 34 having a length of approximately 50 millimeters ±2 millimeters.

The deployment means or mechanism 80 includes a push-pull element or member 81, preferably in the form of a wire 81 with proximal and distal extremities 82 and 83, which is slidably disposed in and extends through the first lumen 26 of the flexible elongate tubular member 22 as hereinafter discussed. The push-pull member 81 is formed of a suitable material such as stainless steel in order optimize torque transmission. The push-pull member 81 has a suitable diameter ranging from approximately 0.005"–0.020", preferably 0.010". In order to provide for optimal torque transmission after being bonded to the Nitinol expansile member 32 as hereinafter discussed, the distal extremity 83 of the push-pull wire 81 provided with a tapered portion 84. The tapered portion 84 has a length ranging from approximately 1.0 centimeters to 6.0 centimeters.

A hypotube connector 101 is provided for joining the tapered portion 84 of the push-pull wire 81 to the is proximal straight portion 73 of the Nitinol wire 61. The hypotube connector 101 has a length ranging from approximately 2.0 centimeters to 4.5 centimeters, an inner diameter ranging from approximately 0.006"–0.008" and an outer diameter ranging from approximately 0.009"–0.012". During manufacture, the tapered portion 84 of the push-pull wire 81 is inserted into one end of the hypotube connector 101 and the proximal end of the straight portion 73 of the Nitinol wire is inserted into the opposite, distal end of the connector 101 whereupon all are bonded together within the hypotube connector 101 utilizing a suitable adhesive such as Loctite™ 648. It should be appreciated that, by grinding and shaping a single length of Nitinol wire, one piece can be utilized having a distal thinner segment which can be shaped into the coil. This obviates the requirement of having a stainless steel push-pull wire, hypotube and connection therebetween.

The proximal end 23 of the flexible elongate tubular member 22 is provided with an expander tube or strain relief member 113 made of a suitable material, such as polycarbonate, having an inner diameter ranging from 0.024"–0.028", an outer diameter ranging from 0.030"–0.036" and a length of approximately 24–26 millimeters. The expander tube 113 is disposed over the proximal end 23 of the tubular member 22 so that the proximal end of the expander tube 113 is positioned approximately 0.5–1.0 millimeters distal to the proximal most end 23 of the tubular member 22 and suitably bonded thereto using an appropriate adhesive such as cyanoacrylite.

As shown in FIGS. 1–3, a stop mechanism or means 121 is provided to control the range of movement or travel of the push-pull wire 81 during deployment and de-deployment of the expansile assembly 31. The stop mechanism 121 comprises first and second, or inner and outer, slidably and rotatably nested, or coaxially carried stop members or handles 122 and 123 which are formed of polycarbonate and mounted as hereinafter discussed.

The inner stop member or handle 122 is formed of a polycarbonate extrusion which, initially, has an outer configuration that is square in cross section and has a dimension ranging from approximately 0.015"–0.050", preferably approximately 0.038". The inner member 122 has a length of approximately 60 millimeters ±5 millimeters and carries a circular in cross section lumen extending therethrough, the lumen having a diameter ranging from approximately 0.010"–0.016". During manufacture, the inner stop member 122 is twisted or turned in order to form a threaded outer surface or helical groove 125 therein which carries pitches of varying degrees or distances. As shown in FIG. 3, the thread 125 carries, preferably, a greater pitch on the proximal segment of the inner handle 122 and a lesser pitch on the distal segment of the inner handle 122.

The distal end of the inner handle 122 carries a collar 124 formed of cyanoacrylite and having a length of approximately 3–5 millimeters and an outer diameter ranging from approximately 0.024"–0.040". The outer collar 124 is coaxially adhesively mounted over the inner handle 122 so that the distal end of the collar 124 is disposed slightly proximal to the distal end of the inner handle tube 122 by several millimeters.

As seen in FIG. 3, an inner handle support hypotube 127 is coaxially, adhesively mounted upon the proximal extremity 82 of the push-pull wire 81 using, preferably, cyanoacrylite so that the proximal end thereof is flush with the proximal most tip of the push-pull wire 81. The support hypotube 127 has an inner diameter ranging from 0.008" to 0.018", preferably approximately 0.012" and an outer diameter ranging from 0.015" to 0.028", preferably approximately 0.020". The inner handle 122 is coaxially, adhesively mounted upon the support hypotube 127, also using an appropriate adhesive such as cyanoacrylite, so that the proximal end 82 of the push-pull wire 81 and the support hypotube 127 carried thereby extend through and proximal of the inner handle 122 as hereinafter discussed.

The outer handle stop member 123 is also constructed of polycarbonate and has a length of approximately 65 millimeters ±5 millimeters, an inner diameter ranging from approximately 0.020"–0.060", preferably approximately 0.055", and an outer diameter ranging from approximately 0.035"–0.080", preferably approximately 0.066". In addition, the proximal end of the outer stop member 123 is provided with a slotted stop segment or inner nut or bushing 126 which has an outer diameter equal to the outer diameter of the outer stop member 123 and which is formed so that the slot 126 is square in shape and has a dimension which is, preferably, approximately 0.042" or slightly larger than the square, outer dimension of the inner handle 122. As shown in FIGS. 1–3, the distal end of the outer handle 123 is secured to the proximal extremity 23 of the elongate tubular member 22 by being adhesively secured to the proximal end of the expander tube 113 using, preferably, an ultra-violet cured adhesive.

As shown in FIGS. 1–3, a freely rotatable handle assembly 131 is provided and carried by the segments of the push-pull wire 81 and inner handle support hypotube 127 extending proximal to the inner handle 122. The rotatable handle assembly 131 comprises a rotatable hypotube casing 132, a rotatable collar 133, a back stop member 134 and a handle grip or sleeve 136 as hereinafter discussed. The complete assembly 131 is sized so as to be capable of being passed through a conventional introducer sheath as hereinafter described. As such, it has a maximum diameter that is no greater than, and, preferably less than, approximately two to three times the diameter of the elongate tubular member 22.

The hypotube casing 132 is of appropriate size, having a length of approximately 15 millimeters, an inner diameter of approximately 0.035" and an outer diameter of approximately 0.042". The hypotube casing 132 is covered with a handle grip or sleeve 136 made of an approximately 15 millimeters length of RNF heat shrink tubing having a thickness of approximately 1/16" and which is applied in a conventional manner.

The rotatable collar 133 is constructed of hypotube having a length of approximately 8 millimeters, an inner diameter of approximately 0.025" and an outer diameter of approximately 0.032". The collar 133 is adhesively, coaxially mounted within the casing 132 using an appropriate adhesive, preferably cyanoacrylite, so that the distal end of the collar 133 is flush with the distal end of the casing 132. The rotatable collar 133 carried by the casing 132 is coaxially rotatably mounted over the proximal end of the inner handle support hypotube 127 as shown in FIGS. 1–3.

A back stop member 134 constructed of stainless steel hypotube and having a length of approximately 4 millimeters, an inner diameter of approximately 0.025" and an outer diameter of approximately 0.032" is adhesively, coaxially mounted (also preferably using cyanoacrylite) on the proximal end of the inner handle support tube 127 proximal to the rotatable collar 133 so that the proximal end of the stop member 134 is flush with the tip of the proximal end of the inner handle support tube 127.

As assembled, the push-pull element 81, with the threaded inner handle member 122 affixed thereto and the collar 124 carried thereby, is movable longitudinally and rotationally within and in relation to the outer handle member 123 which has its distal extremity secured to the expander hypotube 113 carried by the proximal extremity 23 of the polyimide tubular member 22 as hereinbefore discussed. Using the freely rotatable handle assembly 131, it is movable between a forward or distal most position wherein the distal end of the inner handle 122 is engaged with or abutting against the proximal extremity 23 of the polyimide member 22 and the distal end of the rotatable collar 133 abuts against the proximal end of the stop segment 126 of the outer handle member 123 and a rearward or proximal most position wherein the collar 124 is engaged with the stop segment 126 carried by the proximal extremity of the outer member or handle 123 and the proximal end of the rotatable collar 133 abuts against the distal end of the back stop member 134. As hereinafter discussed, these positions correspond to deployed and de-deployed positions and configurations of the expansile assembly 31.

The distal extremity 24 of the flexible elongate tubular member 22 is provided with a hypotube tip 105 over which the membrane 33 is disposed and moves as hereinafter discussed. The hypotube tip 105 is constructed of 304 stainless steel hypotube, or other suitable material, having an outer diameter ranging from approximately 0.028"–0.040" and an inner diameter ranging from 0.024"–0.030" and which is cut to have a length of approximately 3–5 millimeters. The hypotube tip 105 is coaxially mounted over the distal extremity 24 of the polyimide tubular member 22 using, preferably, Loctite so that the tip of the distal extremity 24 of the tubular member 22 is flush with the distal end of the hypotube tip 105.

A tip guide (not shown) is slidably carried by the polyimide tubular member 22 for use as hereinafter discussed. The tip guide is constructed of 1/16" RNF 100 Shrink tubing. The tip guide has a longitudinal axis and a length of approximately 32 millimeters. In addition, the distal portion of the tip guide is provided with a larger, non-shrunk end.

As hereinbefore discussed, the expansile assembly 31 also carries a deformable flexible membrane 33 which is carried by and secured to the distal extremity 24 of the elongate tubular member 22 as shown in FIGS. 1–2.

The membrane 33 is formed of Polyblend™ Extrusion having an internal or inner diameter of 0.020", an outer diameter of 0.036" and which is cut to have a length of approximately 1 centimeter ±1. The proximal end of the membrane 151 is secured to the proximal end of the hypotube tip 105, using an appropriate material such as Loctite 496 adhesive, so that the distal membrane tip 152 extends distal to the tip of the distal extremity 24 of the flexible elongate tubular member 22 and so that distally extending portion of the membrane tip 152 has a length, measured from the distal end of the hypotube tip 105 to the distal end of the membrane tip 152, of approximately 1.0–1.5 millimeters. The extruded membrane tip 152 is subsequently sealed or closed with an extrusion beading 153 as hereinafter discussed.

The beading 153 is made of the same or similar Polyblend material in the form of a solid plug having a diameter of 0.025" and a length of 5 millimeters. This segment of extrusion beading 153 is inserted into the distal, open end of the membrane tip 152 approximately 0.5–0.75 millimeters and heat bonded to the membrane tip 152 so that the distal tip of the beading 153 is flush with the distal end of the membrane tip 152.

Operation and use of the expansile device 21 of the present invention is similar to that disclosed in U.S. Pat. No. 5,782,860, issued Jul. 21, 1998 and U.S. Pat. No. 5,922,009, issued on Jul. 13, 1999, the relevant portions of which are hereby incorporated by reference in their entirety.

Prior to deployment, the expansile member 32 is fully or completely retracted within the distal extremity 24 of the flexible elongate tubular member 22 which causes the expansile member 32 to assume a contracted configuration. Insertion of the device 21 in the contracted configuration into a conventional sheath introducer (not shown) is facilitated by using the tip guide 106 carried by the polyimide tubular member 22 as hereinbefore discussed. Prior to inserting the device 21 into the sheath introducer, the operator slides the tip guide 106 distally, from the middle of the polyimide tubular member 22 to the distal extremity 24 thereof. When the distal end of the tip guide 106 is disposed slightly distal to the distal extremity 24 of the polyimide tubular member 22 and the membrane 33 carried thereby, the distal end of the tip guide 106 is frictionally fit into the conventional one-way valve carried by the sheath introducer, thus urging the valve into a slightly opened position. The distal extremity 24 of the elongate tubular member 22 can then be easily and atraumatically introduced through the valve of the introducer and advanced distally therein until the device is aptly disposed through the tract opening or, in the case of a vascular puncture, in the blood vessel as hereinbefore discussed. By not relying on the tip of the distal extremity 24 of the device 21 to open the valve of the introducer sheath, the integrity of the membrane 33 carried thereby is maintained.

Once appropriately disposed in a tract or puncture site, deployment of the device 21 is accomplished by using the freely rotatable handle assembly 131 to operate the deployment means 80 to move the push-pull wire 81 distally to urge the expansile member 32 distally out of the lumen 26 of the flexible elongate tubular member 22, into the membrane 33. As soon as the distal part of the expansile member 32 clears the lumen 26, it begins an attempt to expand into its shape memory, predetermined, or free configuration which corresponds to the ellipsoidal, helical coil configuration 34. However, as hereinafter discussed, the expansile member 32 is prevented from fully expanding into its free shape configuration as a result of the membrane 33 partially constraining the expansion process.

More specifically, the distal coil 71 operates to expand the membrane 33 initially to a small degree. This initial process avoids sudden gross distortion of the membrane 33. As soon as the expansile member 32 moves further distally out of the lumen 26 and expands into the membrane 33, the non-adherent portion of the membrane 33, distal to the portion of membrane 33 fixed to the distal extremity 24 of the elongate tubular member 22, preferentially begins to move and assume the planar configuration due to the lubricious surface of the hypotube tip 105 and the ease with which the membrane 33 slides thereupon. Expansion proceeds with the middle coil 69 causing the membrane 33 to expand to its desired size. The proximal coil 68 expands last, to centralize and stabilize the configuration so that the push-pull wire 81 is centered with respect to the middle coil 69 and the fully expanded membrane 33.

Throughout the deployment process, as the coil 34 is expanding and seeking its memorized configuration it is rotating in a leftward or counter-clockwise direction. As a result, the push-pull member 81 is being torqued by the slightly rotating coil 34 in the same direction. This torque requires that the push-pull member 81 be permitted to rotate counter-clockwise in order for the coil 34 to operatively rotate and expand within, and without damaging, the membrane 33 as hereinafter discussed. Furthermore, the amount of torque developed by the expanding coil 34 varies so that more torque is developed and, therefore, more rotation of the push-pull member 81 is optimal, during deployment of the distal portion of the coil 34. In all, the push-pull member 81 rotates approximately 1 to 3, preferably approximately 1.5 to 2, revolutions. As hereinafter discussed, when the operator pushes the freely rotatable handle 131 distally, the variable pitch threaded inner handle 122 effects such a counter-clockwise, controlled, torqued deployment.

The counter-clockwise rotation during deployment is provided and controlled by rotation means or mechanism which comprises the threaded 125 portion of the inner handle 122 traveling longitudinally and rotationally through the square shaped inner bushing or nut 126 of the outer handle member 123. The lesser or tighter pitch of the thread 125 at the distal segment of the inner handle 122 causes greater rotation during deployment of the distal coil 71. It should be appreciated that the direction of rotation of the expansile member depends upon the orientation in which the coil is manufactured. It is, therefore, only important that the rotation means be manufactured to provide controlled rotation in the same direction as that which the coil seeks during expansion according to its manufactured orientation.

Furthermore, the hypotube casing 132 and the rotatable collar 133 enable the operator to ergonomically and stably maintain a hand-hold on the handle 131 of the device 21 during operation thereof without having to remove his or her hand in order to accommodate or permit rotation of the inner handle member 122. This is effected by the free rotation of the inner handle support tube 127, the push-pull member 81 and the back stop member 134 within the casing 132 and rotatable collar 133. That is, the handle assembly 131 accommodates rotation of the deployment means 80 and expansile member 32 without, or independent of, the portions of the handle assembly 131 held by the operator.

During expansion of the expansile member 32 the membrane 33 covering the coil 34 simultaneously constrains the coil 34, thus exerting counteractive or countervailing contractile forces on the expanding coil 34 which is seeking its memorized, ellipsoidal, bi-conical, free or unconstrained configuration. Thus, the membrane 33 does not expand passively. Rather, the expanding coil 34 forcibly expands the membrane 33 to cause the non-planar turns or coils 68, 69 and 71 of the coil 34 to assume a substantially planar or disk-like configuration with the membrane 33 being taut and disposed on opposite sides of the expansile member 32 to form an expansile assembly 31 which when expanded is generally perpendicular to the longitudinal axis of the first flexible elongate tubular member 22. The expansile member 32, when so deployed into this constrained, partially expanded configuration, is sufficiently rigid and robust so as to provide a supporting framework for the membrane 33 to keep it taut and capable of occluding an opening. In addition, deployment of the expansile assembly 31 is effected without obstructing or impinging on walls of the smallest openings in the body due to the uniquely small profile and expansion mechanics of the helical coil 34 during deployment and de-deployment as hereinbefore discussed.

Figure 6:
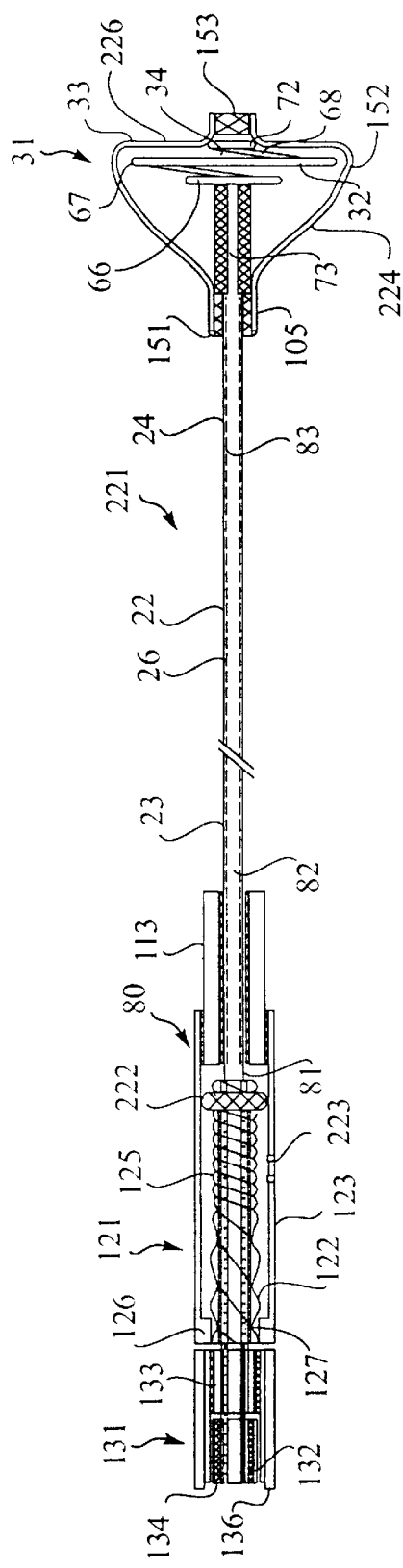
FIG. 6 is a side-elevational view partially in section of another embodiment of the device of the present invention without the tip guide and having the expansile member in the expanded configuration.
Figure 7:
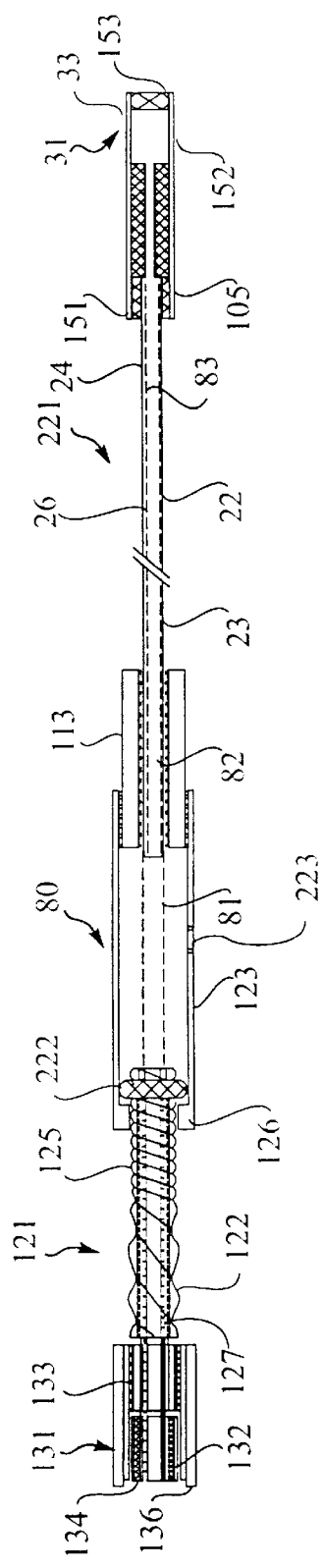
FIG. 7 is a side-elevational view partially in section of the device in FIG. 6 with the expansile assembly in a de-deployed or contracted configuration.

Another embodiment of the expansile device of the present invention is shown in FIGS. 6 and 7. Device 221 is similar to device 21 with the principle difference being in the expanded configuration of device 221. Thus all parts of closure device 221 that are identical to those of device 21 carry the same numbers as those of the closure device 21. In addition, device 221 is provided with means for urging the membrane 33 into a partially convex configuration during movement of expansile member 32 between contracted and expanded configurations to seal a puncture. Inner handle 122 of device 221 carries a piston 222 which replaces collar 124 in device 21. Piston 222 is made of any suitable material, preferably a compressible or deformable silicone O-ring, and is of an appropriate diameter slightly larger than the inner diameter of outer handle 123. Piston or O-ring 222 is mounted to inner handle 122 in an appropriate manner similar to that hereinbefore described for collar 124 of device 21. Outer handle 123 is provided with a small transverse hole 223 located at a predetermined, appropriate point along the longitudinal axis of outer handle 123. Hole 223 has an appropriate diameter ranging from approximately 0.005–0.050 inches, preferably approximately 0.020 inches.

Operation and use of device 221 is the same as that of device 21.

The primary difference between device 21 and device 221 is the configuration that membrane 33 assumes during deployment, when expansile assembly 31 is in the fully expanded configuration, occluding or sealing a vascular puncture. During deployment of device 221, as inner handle 122 rotates and slides distally within outer handle 123, piston 222 maintains a substantially air-tight seal between inner and outer handles 122 and 123. Thus, as long as piston 222 is disposed proximal of hole 223, air naturally contained between inner and outer handles 122 and 123 and within lumen 26 of elongate tubular member 22 is displaced or vented out of outer handle 123 through hole 223 as inner handle 122 moves distally. When piston 222 becomes disposed distal of hole 223, continued distal movement of inner handle 122 within outer handle 123 forcibly displaces a predetermined volume of air, retained both in between inner and outer handles 122 and 123 and within lumen 26 of elongate tubular member 22, into membrane 33.

As hereinbefore described in conjunction with device 21, during expansion of device 221, the non-adherent portion of membrane 33, distal to the portion of membrane 33 fixed to distal extremity 24 of elongate tubular member 22, begins to move preferentially. With the compression and introduction of the small quantity of air from lumen 26, the deployment of coil 34 into membrane 33 causes the proximal outer surface 224 of membrane 33 to assume a substantially different configuration from the distal outer surface 226 of membrane 33 as seen in FIG. 1. The taper of proximal outer surface 224 assumes a substantially convex configuration in the expanded configuration instead of the substantially disk-like configuration of the proximal side of membrane 33 in expanded device 21. Similar to membrane 33 of device 21, distal outer surface 226 of membrane 33 of device 221 maintains a disk-like configuration when device 221 is in the fully expanded configuration within the vascular puncture.

Due to the durometer of the membrane material, the alteration in taper of proximal outer surface 224 of membrane 33 of device 221 occurs at pressures very close to the mean arterial pressure of a human patient. Thus, the disk-like configured distal outer surface 226 of membrane 33 of expansile assembly 31 is naturally urged or forced laterally by arterial blood flow within the vessel, towards the inner wall of the vessel whereby the tapered proximal outer surface 224 is caused to more tightly occlude the puncture in the wall of the vessel without the expansile assembly 31 obstructing ongoing blood flow.

Another embodiment of the expansile device of the present invention is shown in FIG. 8. Device 231 is similar to device 221 with the principle difference being in the expanded configuration of device 231. Thus all parts of closure device 231 that are identical to those of device 221 carry the same numbers as those of the closure device 221. In addition, device 231 is provided with means for urging the proximal outer surface 224 of membrane 33 into a convex configuration during movement of expansile assembly 31 between contracted and expanded configurations that is distinct from the urging means of device 221. Expansile member 32 is provided with an additional proximal coil 232. Additional proximal coil 232 is of substantially equal size and diameter to proximal coil 66. In the free or unconstrained configuration of helical coil 34, proximal coils 66 and 232 lie immediately adjacent to one another like two coils of a tightly wound spring. Thus, the overall unconstrained configuration and size of coil 34 is essentially unchanged from that of device 221.

Operation of device 231 is substantially the same as that of device 21 with the main difference being in the expanded configuration which device 231 assumes. In addition, second proximal coil 232 requires that, in order to be fully deployed, device 231 be provided with a slightly increased stroke length (not shown). During movement of the expansile member 32 from the contracted to the expanded configuration, due to the additional stiffness and bulk provided by tightly apposed proximal coils 66 and 232, the proximal outer surface 224 of membrane 33 is tented or tapered between the two coils 66 and 232 and assumes a substantially convex configuration as opposed to the substantially disk-like configuration of both sides of membrane 33 assumed by device 21 in the expanded configuration. Double coils 66 and 232 stretch or unwind less when tension is applied to fully deployed device 231. Thus, proximal outer surface 224 of membrane 33 is more firmly supported when device 231 is under tension. In addition, as shown in FIG. 8*b*, depending on the stiffness provided the proximal coils 66 and 232, they can be made to separate slightly under tension so that during deployment of device 231, proximal coil 66 remains inside and up against the inner vessel wall of the puncture while proximal coil 232 is made to pull proximally, through the arteriotomy or puncture in the vessel, and come to rest on the outer wall thereof. In this manner the inner and outer walls of the artery are, essentially, sandwiched or gently compressed between proximal coils 66 and 232 whereupon any additional external proximal tension may be eliminated or discontinued. This is particularly useful for larger arteriotomies or punctures.

It is apparent from the foregoing that there has been provided an expansile device for use in blood vessels and tracts in the human body and more particularly for percutaneous occlusion of vascular access sites in the human body and method of using and manufacturing the same.

Although the expansile device and method have been described principally in use with the human body it should be appreciated that the expansile device and method also can be utilized with animals in a similar manner.

In addition, it should be appreciated that the expansile device can be used within many different natural and iatrogenically created tracts in the body in order to provide for other therapeutic or prophylactic modalities.

Thus, it is also apparent from the foregoing that there has been provided a expansile device and method for percutaneous access and occlusion of openings and tracts in the human body that have distinct advantages over those heretofore provided.

What is claimed:

1. A device for expansion within a blood vessel having a wall defining a lumen in the body comprising an elongated tubular member having proximal and distal extremities and having a longitudinal axis, an expansile member carried by the distal extremity of the elongated tubular member and movable between contracted and expanded configurations, a deformable membrane having proximal and distal outer surfaces at least partially covering the expansile member in the expanded configuration, said proximal and distal outer surfaces having substantially different configurations when the expansile member is in the expanded configuration, deployment means carried by the proximal extremity of the elongated tubular member and coupled to the expansile member for moving the expansile member between the contracted and expanded configurations and a handle assembly carried by the proximal extremity of the elongated tubular member and coupled to said deployment means.

2. The device of claim 1 wherein the proximal outer surface of said deformable membrane has a substantially convex configuration when the expansile member is in the expanded configuration.

3. The device of claim 2 wherein the distal outer surface of said deformable membrane has a substantially disc shape configuration when the expansile member is in the expanded configuration.

4. The device of claim 2 further including means for urging the proximal outer surface of the membrane into said convex configuration during movement of the expansile member between contracted and expanded configurations.

5. The device of claim 4, wherein said handle assembly extends along a longitudinal axis and includes inner and outer members, said inner member being slidably carried within said outer member and said urging means includes a piston carried by the inner member and a transverse hole carried by the outer member at a predetermined point along the longitudinal axis of the handle assembly so that, when said piston moves distal of said hole during movement of the expansile member between the contracted and expanded configurations, a predetermined amount of air contained within said elongate tubular member enters said membrane whereby the proximal outer surface assumes said convex configuration.

6. The device of claim 4 wherein said expansile member is comprised essentially of a superelastic material having a free state and having a configuration in the free state which has a larger size then said expanded configuration and said membrane is formed to permit movement of the expansile member within the membrane and to constrain said expansile member from the free state configuration into said smaller expanded configuration during movement between contracted and expanded configurations.

7. The device as in claim 6 wherein said configuration in a free state is a bi-conical coil-like configuration having proximal, middle and distal turns which are non-planar with respect to one another, said proximal and distal turns being of substantially equal size and said middle turn being larger than said proximal and distal turns.

8. The device as in claim 7, said urging means further including the bi-conical coil-like configuration having at least two proximal turns wound tightly together and being of substantially equal size so that, during movement of the expansile member from the contracted to the expanded configuration, the proximal outer surface of the membrane assumes said convex configuration.

\* \* \* \* \*